United States Patent
Grashow et al.

(10) Patent No.: US 12,257,388 B2
(45) Date of Patent: Mar. 25, 2025

(54) NASAL PILLOWS CUSHION FOR PATIENT INTERFACE DEVICE

(71) Applicant: KONINKLIJKE PHILIPS N.V., Eindhoven (NL)

(72) Inventors: Jonathan Sayer Grashow, Pittsburg, PA (US); Robert Edward O'Grady, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/372,177

(22) Filed: Sep. 25, 2023

(65) Prior Publication Data

US 2024/0009418 A1     Jan. 11, 2024

Related U.S. Application Data

(63) Continuation of application No. 17/032,474, filed on Sep. 25, 2020, now Pat. No. 11,819,613.

(60) Provisional application No. 62/907,186, filed on Sep. 27, 2019.

(51) Int. Cl.
    *A61M 16/00*     (2006.01)
    *A61M 16/06*     (2006.01)

(52) U.S. Cl.
    CPC .... *A61M 16/0622* (2014.02); *A61M 16/0666* (2013.01); *A61M 2210/0618* (2013.01)

(58) Field of Classification Search
    CPC ............ A61H 1/008; A61H 2201/0153; A61H 2201/105; A61H 2205/04; A61H 2205/081; A61M 16/0622; A61M 16/0666; A61M 2210/0618
    See application file for complete search history.

(56) References Cited

U.S. PATENT DOCUMENTS

| | | |
|---|---|---|
| 8,573,201 B2 | 11/2013 | Henry |
| 8,985,117 B2 | 3/2015 | Gunaratnam |
| 9,032,955 B2 | 5/2015 | Lubke |
| 9,220,860 B2 | 12/2015 | Davidson |
| 9,480,809 B2 | 11/2016 | Cameron |
| 9,884,555 B2 | 2/2018 | Tran |
| 10,376,666 B2 | 8/2019 | McAuley |
| 10,953,179 B2 | 3/2021 | Siew |

(Continued)

OTHER PUBLICATIONS

International Search Report for PCT/EP2020/076807 dated Sep. 24, 2020.

*Primary Examiner* — Margaret M Luarca
*Assistant Examiner* — Sarah B Lederer
(74) *Attorney, Agent, or Firm* — Michael W. Haas

(57) ABSTRACT

A cushion for use in providing a regimen of respiratory therapy to a patient includes a base that defines a main cavity therein an aperture for receiving a flow of breathing gas. A pair of nasal pillows each extend from the base, each having a cone-shaped head that tapers inward and upward from a base portion, that extends directly from the base, to a top opening. Each head is formed to engage an inner portion of a nare of the patient. Each head defines a passage extending between the main cavity and the top opening for further conveying the flow of breathing gas from the main cavity to a nasal passage of the patient. Each base portion includes an inner edge positioned near the center of the cushion that merges with the hollow base and an opposite outer edge spaced upward from an outer surface of the hollow base.

18 Claims, 5 Drawing Sheets

(56) References Cited

U.S. PATENT DOCUMENTS

| | | |
|---|---|---|
| 11,679,222 B2 | 6/2023 | Dantanarayana |
| 11,819,613 B2* | 11/2023 | Grashow ........... A61M 16/0666 |
| 2006/0266361 A1 | 11/2006 | Hernandez |
| 2011/0073116 A1* | 3/2011 | Genger ............. A61M 16/0677 |
| | | 128/207.18 |
| 2016/0095996 A1 | 4/2016 | Baecke |
| 2016/0296720 A1 | 10/2016 | Barbara |
| 2018/0099113 A1 | 4/2018 | Bell |
| 2019/0117923 A1* | 4/2019 | Downey ........... A61M 16/0666 |

* cited by examiner

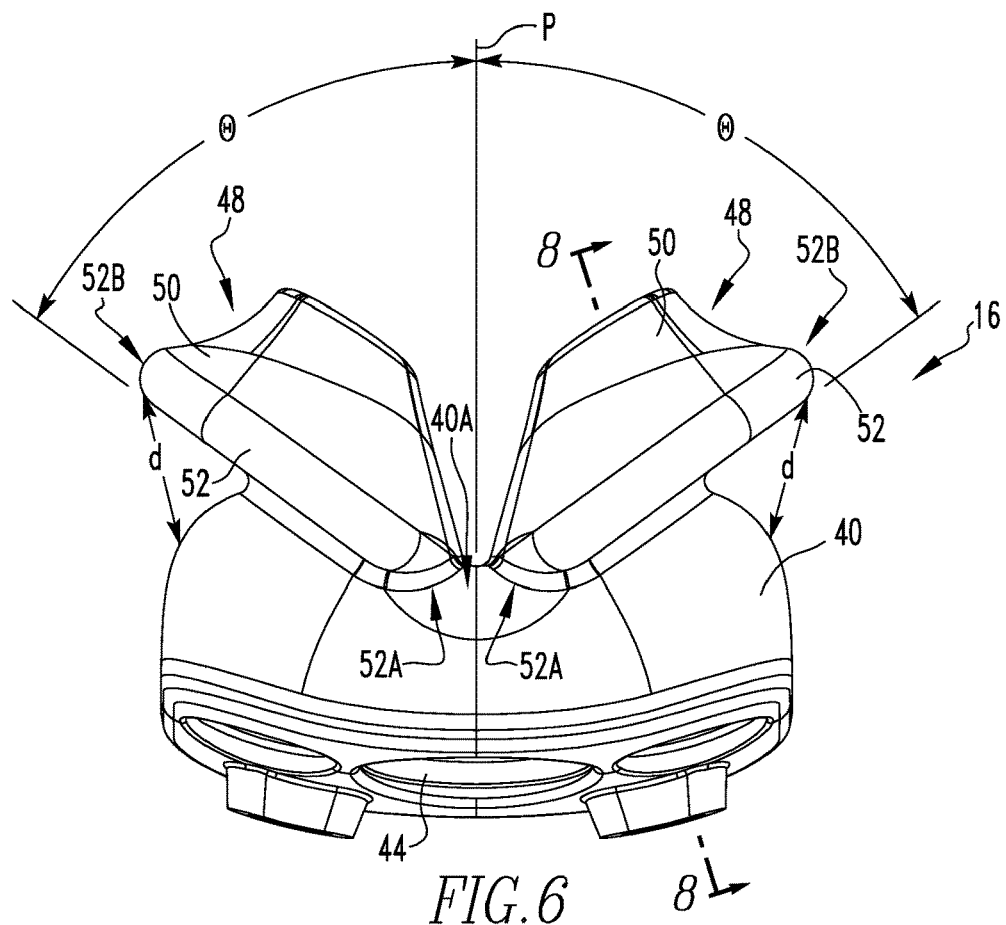
FIG.6
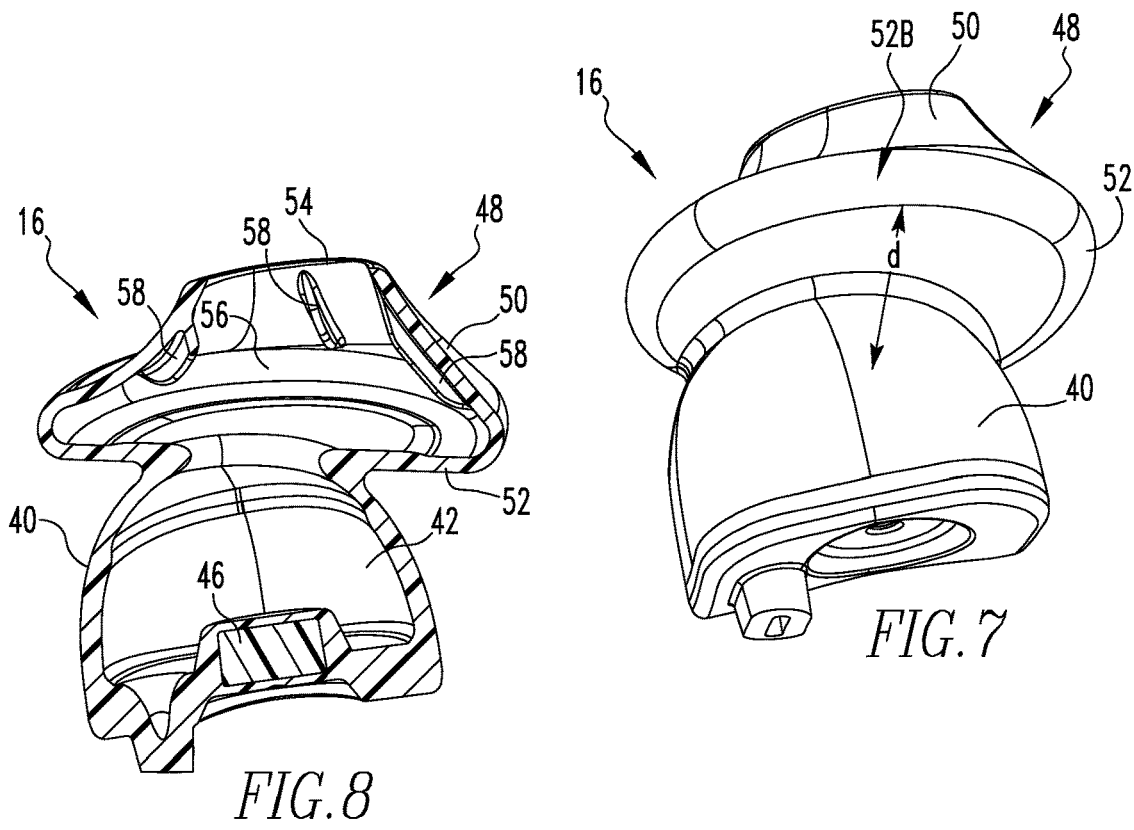
FIG.8
FIG.7

NASAL PILLOWS CUSHION FOR PATIENT INTERFACE DEVICE

CROSS-REFERENCE TO RELATED APPLICATIONS

This patent application is a Continuation of U.S. patent application Ser. No. 17/032,474, filed Sep. 25, 2020, which claims the priority benefit under 35 U.S.C. § 119(e) of U.S. Provisional Application No. 62/907,186, filed on Sep. 27, 2019, the contents of which are herein incorporated by reference.

BACKGROUND OF THE INVENTION

1. Field of the Invention

The present invention generally relates to patient interface devices for use in pressure support systems that supply a flow of gas to the airway of a patient and, more particularly, to nasal pillows cushions for use in such patient interface devices.

2. Description of the Related Art

Obstructive sleep apnea (OSA) is a condition that affects millions of people from around the world. OSA is characterized by disturbances or cessation in breathing during sleep. OSA episodes result from a partial or complete blockage of airflow during sleep that lasts at least 10 seconds and often as long as 1 to 2 minutes. In a given night, people with moderate to severe apnea may experience complete or partial breathing disruptions as high as 200-500 per night. Because their sleep is constantly disrupted, they are deprived of the restorative sleep necessary for efficient functioning of body and mind. This sleep disorder has also been linked with hypertension, depression, stroke, cardiac arrhythmias, myocardial infarction and other cardiovascular disorders. OSA also causes excessive tiredness.

One method for treating OSA is positive airway pressure (PAP) therapy. Known PAP therapies include continuous positive airway pressure (CPAP), wherein a constant positive airway pressure is provided to the airway of the patient in order to splint the patient's airway open, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient.

Because patient interface devices are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. Another concern is that an improperly fitted patient interface device can include gaps between the patient interface device and the patient that cause unwanted leakage. Thus, it is desirable to select a patient interface device that properly fits a patient.

One type of patient interface device is a nasal pillows mask. Typically, nasal pillows masks use a silicone sealing cushion having a pair of heads, each in the shape of a truncated cone that is inserted into a respective nostril of a patient and seals against the interior and exterior surfaces of the nostril opening. Current designs also comprise a hollow stalk which connects to the bottom of the cone-shaped head on one end and extends to an elastomeric base membrane on the other end, thus spacing the entire cone-shaped head from the base membrane. Air travels from the cushion base, through the cylindrical stalk, and into the head as the patient inhales. Stalks allow the cone-shaped heads to move and rotate with respect to the cushion base, improving the ability of the cushion to conform to variations in a patient's facial geometry and allowing the cone-shaped heads to stay in contact with a patient's nose even if the cushion base moves a small amount (e.g. when cushion base contacts bedding as patient rolls over in bed). The stalks in current pillows designs allow the head to articulate with respect to the cushion base, but they also have some disadvantages. For instance, stalks add extra size, bulk, and weight to the cushion. This is especially problematic since nasal pillows masks are typically constructed to be the smallest/lightest masks on the market. Stalks also add extra airflow resistance. The small diameters of cylindrical stalks add airflow resistance and reduces breathing comfort for the patient.

SUMMARY OF THE INVENTION

As one aspect of the present invention a cushion for use in providing a regimen of respiratory therapy to a patient comprises: a hollow base defining a main cavity therein, the hollow base defining at least one aperture for receiving a flow of breathing gas generated by a pressure generating device; a pair of nasal pillows each extending from the hollow base, each nasal pillow having a generally cone-shaped head that tapers inward and upward from a base portion, that extends directly from the base, to a top opening, wherein each cone shaped head is structured to sealingly engage an inner portion of a nare of the patient with the top opening thereof positioned within the nare of the patient, wherein each cone-shaped head defines a passage therethrough that extends between the main cavity and the top opening and is structured to further convey the flow of breathing gas from the main cavity to a nasal passage of the patient, and wherein each base portion includes an inner edge positioned near the center of the cushion that merges with the hollow base and an opposite outer edge that is disposed at an outer portion of the cushion and spaced a distance upward from an outer surface of the hollow base.

Each base portion may be positioned at an angle relative to a central reference plane bisecting the cushion, and the angle may be in the range of 45-90 degrees.

The hollow base and the pair of nasal pillows may each be portions of a single unitary member.

A region where the inner edge of each base portion and the hollow base merge may be at least one of: a lessor thickness than a wall of the hollow base adjacent thereto or formed of a softer material than the hollow base adjacent thereto.

The at least one aperture may comprise a first aperture disposed at a first end of the hollow base and a second aperture disposed at an opposite second end of the hollow base.

Each cone-shaped head may include a number of ribs that each extend from an inner surface of the cone-shaped head partially into the passage defined therein.

As another aspect of the present invention, a patient interface device for use in providing a regimen of respiratory therapy to a patient comprises: a frame structured to be coupled to the head of the patient by a headgear; and a cushion coupled to the frame, the cushion comprising: a hollow base defining a main cavity therein, the base defining at least one aperture for receiving a flow of breathing gas generated by a pressure generating device; a pair of nasal pillows each extending from the hollow base, each nasal pillow having a generally cone-shaped head that tapers inward and upward from a base portion, that extends directly from the hollow base, to a top opening, wherein each cone shaped head is structured to sealingly engage an inner portion of a nare of the patient with the top opening thereof positioned within the nare of the patient, wherein each cone-shaped head defines a passage therethrough that extends between the main cavity and the top opening and is structured to further convey the flow of breathing gas from the main cavity to a nasal passage of the patient, and wherein each base portion includes an inner edge positioned near the center of the cushion that merges with the hollow base and an opposite outer edge that is disposed at an outer portion of the cushion and spaced a distance upward from an outer surface of the hollow base.

Each base portion may be positioned at an angle relative to a central reference plane bisecting the cushion, and the angle may be in the range of 45-90 degrees.

The hollow base and the pair of nasal pillows may each be portions of a single unitary member.

A region where the inner edge of each base portion and the base merge may be at least one of: a lessor thickness than a wall of the hollow base adjacent thereto or formed of a softer material than the hollow base adjacent thereto.

The at least one aperture may comprise a first aperture disposed at a first end of the hollow base and a second aperture disposed at an opposite second end of the hollow base.

Each cone-shaped head may include a number of ribs that each extend from an inner surface of the cone-shaped head partially into the passage defined therein.

As yet another aspect of the present invention, a system adapted to provide a regimen of respiratory therapy to a patient comprises: a pressure generating device structured to generate a flow of breathing gas; a delivery conduit having a first end coupled to the pressure generating device and an opposite second end; and a patient interface device comprising: a frame structured to be coupled to the head of the patient by a headgear; and a cushion coupled to the frame, the cushion comprising: a hollow base defining a main cavity therein, the hollow base defining at least one aperture for receiving a flow of breathing gas generated by the pressure generating device from the second end of the deliver conduit; and a pair of nasal pillows each extending from the hollow base, each nasal pillow having a generally cone-shaped head that tapers inward and upward from a base portion, that extends directly from the hollow base, to a top opening, wherein each cone shaped head is structured to sealingly engage an inner portion of a nare of the patient with the top opening thereof positioned within the nare of the patient, wherein each cone-shaped head defines a passage therethrough that extends between the main cavity and the top opening and is structured to further convey the flow of breathing gas from the main cavity to a nasal passage of the patient, and wherein each base portion includes an inner edge positioned near the center of the cushion that merges with the hollow base and an opposite outer edge that is disposed at an outer portion of the cushion and spaced a distance upward from an outer surface of the hollow base.

The at least one aperture may comprise a first aperture disposed at a first end of the hollow base and a second aperture disposed at an opposite second end of the hollow base.

Each cone-shaped head may include a number of ribs that each extend from an inner surface of the cone-shaped head partially into the passage defined therein.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 6 is a rear elevation view of the cushion of FIG. 1;

FIG. 7 is a side elevation view of the cushion of FIG. 1;

FIG. 8 is an elevation sectional view of the cushion of FIG. 1 taken along line 8-8 of FIG. 6.

DETAILED DESCRIPTION OF EXEMPLARY EMBODIMENTS

Figure 1:
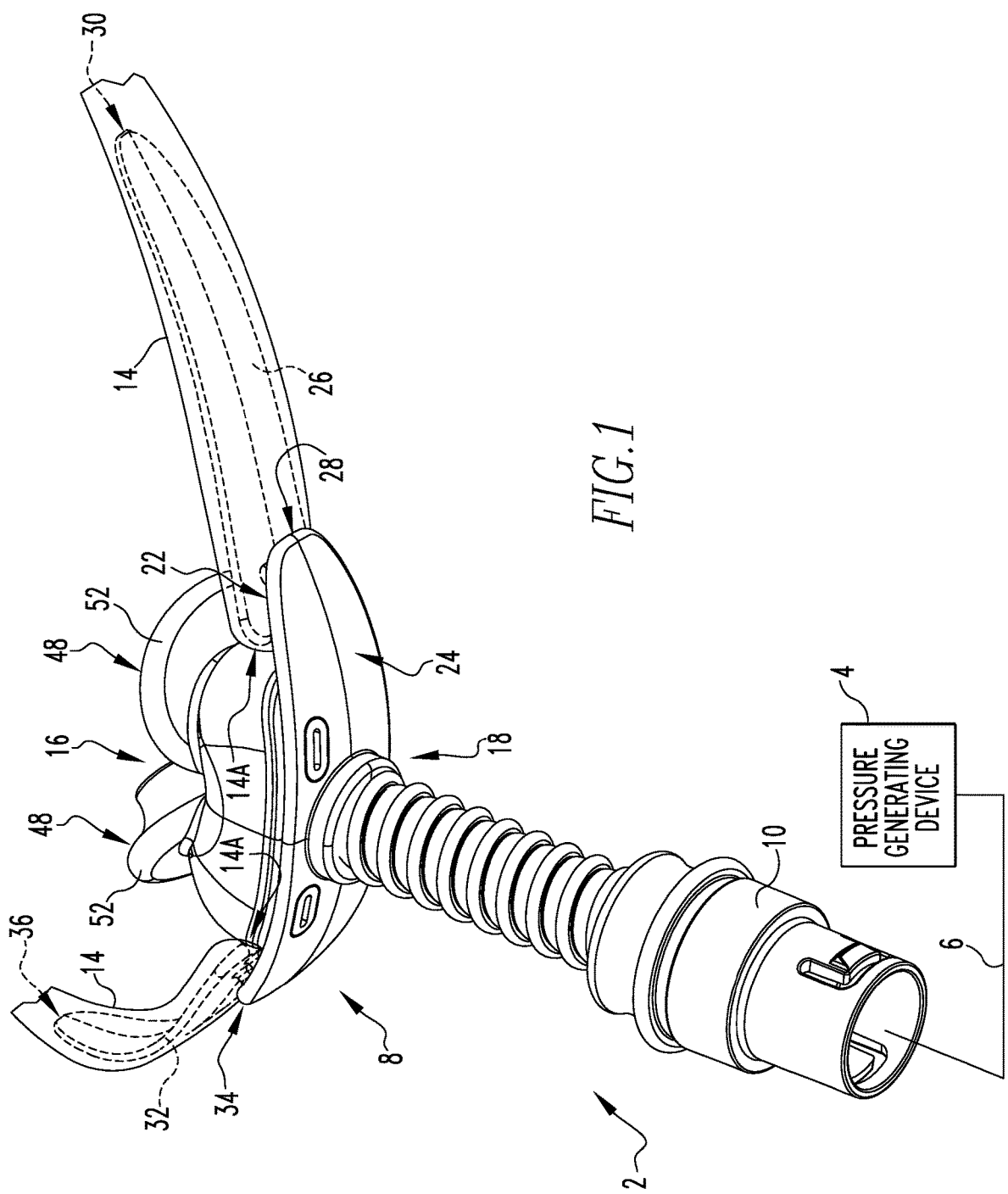
FIG. 1 is a partially schematic perspective view of a system adapted to provide a regimen of respiratory therapy to a patient including a patient interface device having a cushion according to one exemplary embodiment of the present invention.
Figure 2:
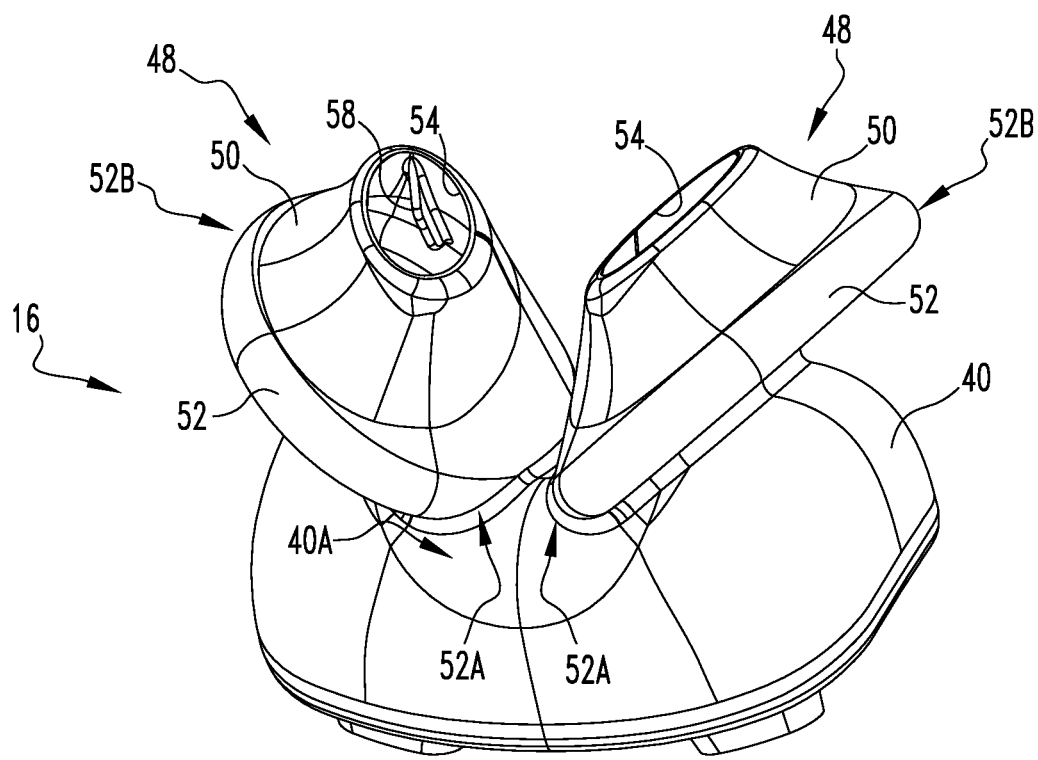
FIG. 2 is a front perspective view of the cushion of FIG. 1.
Figure 3:
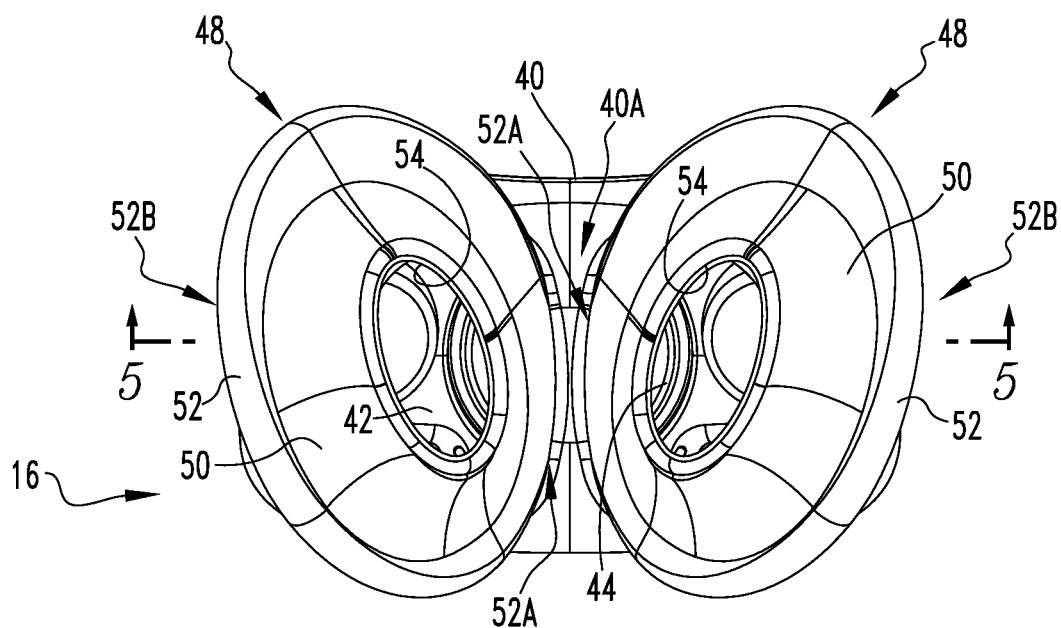
FIG. 3 is a top view of the cushion of FIG. 1.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the statement that two or more parts or components "engage" one another shall mean that the parts exert a force against one another either directly or through one or more intermediate parts or components. As employed herein, the term "number" shall mean one or an integer greater than one (i.e., a plurality). Directional phrases used herein, such as, for example and without limitation, left, right, upper, lower, front, back, on top of, and derivatives thereof, relate to the orientation of the elements shown in the drawings and are not limiting upon the claims unless expressly recited therein. As employed herein, the term "and/or" shall mean one or both of the elements separated by such term. For example, "A and/or B" would mean any of: i) A, ii) B, or iii) A and B.

A system 2 adapted to provide a regimen of respiratory therapy to a patient according to one exemplary embodiment of the invention is generally shown in FIG. 1. System 2 includes a pressure generating device 4 (shown schematically), a delivery conduit 6 (shown schematically), a patient interface device 8 having a fluid coupling conduit 10 coupled via a conduit segment 12, and a headgear (only straps 14 thereof are shown). Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pennsylvania), and auto-titration pressure support devices. Delivery conduit 6 is structured to communicate the flow of breathing gas from pressure generating device 4 to patient interface device 8 through fluid coupling conduit 10 and conduit segment 12. In the exemplary embodiment illustrated in FIG. 1, fluid coupling conduit 10 is a straight connector, however, it is to be appreciated that other suitable couplings may be employed without varying from the scope of the present invention. It is also to be appreciated that conduit segment 12 may be eliminated, and thus delivery conduit 6 connected directly to patient interface device 8 or connected via an aforementioned coupling without varying from the scope of the present invention. Delivery conduit 6 and patient interface device 8 are often collectively referred to as a patient circuit.

A BiPAP© device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, flow/pressure generating device 4 is also referred to as a gas flow generating device, because flow results when a pressure gradient is generated. The present invention contemplates that flow/pressure generating device 4 is any conventional system for delivering a flow of gas to an airway of a patient or for elevating a pressure of gas at an airway of the patient, including the pressure support systems summarized above and non-invasive ventilation systems.

Continuing to refer to FIG. 1, patient interface device 8 includes a cushion 16 coupled to a frame 18 via a magnetic arrangement, discussed further below. Cushion 16 may be formed of any pliable material (e.g., without limitation, silicone). Frame 18 may be formed of a substantially rigid material (e.g., without limitation, one or more plastics). Frame 18 includes a central portion 20 formed as a generally thin member having a patient facing side 22 and an opposite outward facing side 24. Central portion 20 is curved such that patient facing side 22 is generally concave-shaped, while outward facing side 24 is generally convexly-shaped. Frame 18 further includes a first wing portion 26, which extends generally from a first end 28 of central portion 20 in a slightly tapering manner to a first distal tip 30; and a second wing portion 32, which extends generally from a second end 34 of central portion 20 in a slightly tapering manner to a second distal tip 36. In the example embodiment illustrated in FIG. 1, each of first and second wing portions 26 and 32 are each offset a distance from patient facing side 22 of central portion 20 by a respective spacer portion which are each of narrower dimensions than the portions of central portion 20 and wing portions 26 and 32 immediately adjacent thereto.

Each wing portion 26 and 32 is structured to cooperatively engage a respective one of headgear straps 14 in a manner that secures each strap 14 to frame 18. More particularly, each strap 14 is formed from an elastic fabric material as a generally flattened tubular member having a closed leading end 14A. An aperture which provides access to the inner portion of each flattened tubular member is defined in each strap 14 a distance from closed leading end 14A thereof. To secure a strap 14 to frame 18, distal portion 30 of wing portion 26 is inserted into the aperture of one strap 14. The aperture is then slid along wing portion 26 until an outward facing portion of the perimeter of the aperture contacts the spacer portion. At such time, the majority of wing portion 26 is positioned inside the flattened tubular member which is strap 14. Next, the aperture is generally stretched around the remaining portion of wing portion 26 such that the previously remaining portion of wing portion 26 is positioning in the portion of the flattened tubular member generally between the aperture and sealed end 14A. When fully installed, the aperture of strap 14 is disposed encircling the spacer portion between central portion 20 and wing portion 26. The other strap 14 is likewise secured to frame 18 by repeating the same steps with second wing portion 32.

Referring now to FIGS. 2-8, details of cushion 16 will now be described. Cushion 16 includes a generally hollow base 40 that defines a main cavity 42 therein. Base 40 includes at least one aperture 44 for receiving a flow of breathing gas generated by pressure generating device 4 into main cavity 42, such as previously discussed in regard to FIG. 1. In the example embodiment illustrated in FIGS. 1-8, base 40 includes a number of magnetic elements 46 disposed in a lower portion thereof that are positioned to magnetically couple to corresponding magnetic elements provided in frame 18 so as to selectively couple cushion 16 to frame 18, such as shown in FIG. 1.

Continuing to refer to FIGS. 2-8, cushion 16 further includes a pair of nasal pillows 48, each extending directly from base 40. More particularly, each nasal pillow 48 includes a generally cone-shaped head 50 that tapers inward (without flaring outward) and upward from a base portion 52 (that extends directly from base 40) to a top opening 54. Each cone shaped head 50 is tapered so as to be shaped to sealingly engage an inner portion of a nare of a patient with top opening 54 thereof positioned within the nare of the patient. Each cone-shaped head 50 defines a passage 56 therethrough that extends between main cavity 42 and top opening 54 and is structured to further convey the flow of breathing gas from main cavity 42 to a nasal passage of the patient. As shown in the section views of FIGS. 5 and 8, each nasal pillow 48 may include one or more ribs 58 that extend from an inner surface of cone-shaped head 50 partially into passage 56 defined therein in a direction roughly normal to the inside surface of each cone-shaped head 50. Such ribs 58 serve to stiffen each cone-shaped head 50 so as to resist collapse when in contact with the nostril of a patient. Such ribs 58 are advantageous for this purpose (e.g. compared to thickening the wall or using a stiffer material) because they selectively stiffen the pillow against collapse while still allowing the pillow to deform circumferentially to match the shape of the nostril. Ribs 58 may be spaced around the inner perimeter of each cone-shaped head 50. In an example embodiment, ribs 50 are spaced away from the portion of each cone-shaped head 50 that is structured to engage at or near the nasal septum of the patient as such area is generally sensitive and thus undesirable to have stiffened.

Figure 4:
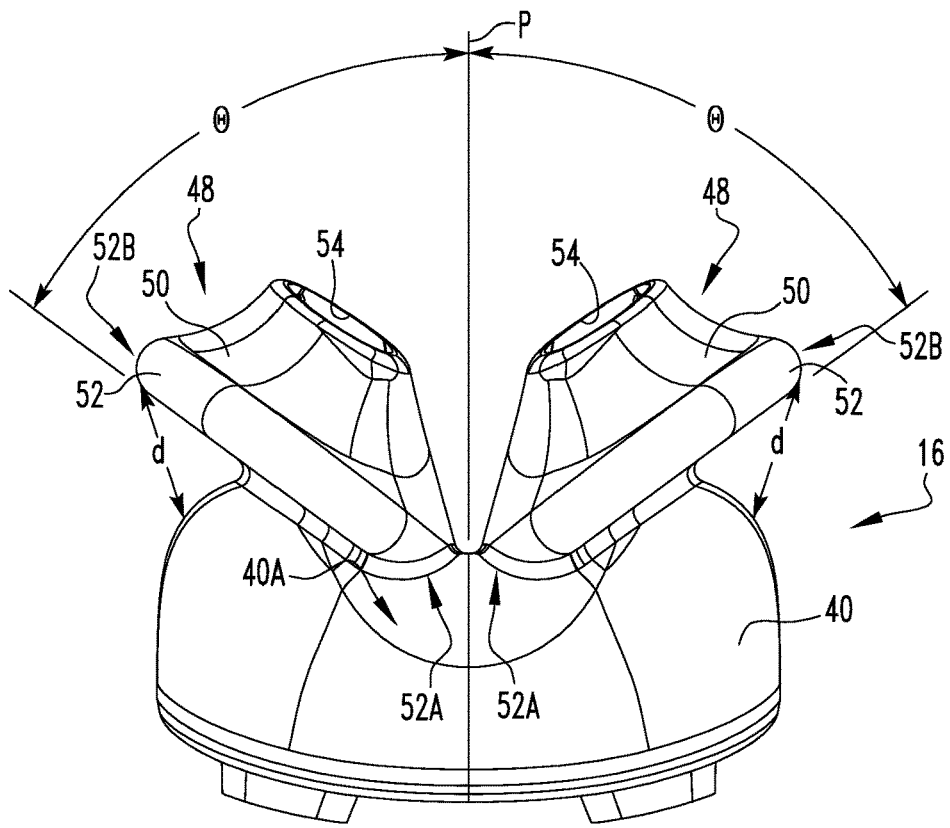
FIG. 4 is a front elevation view of the cushion of FIG. 1.
Figure 5:
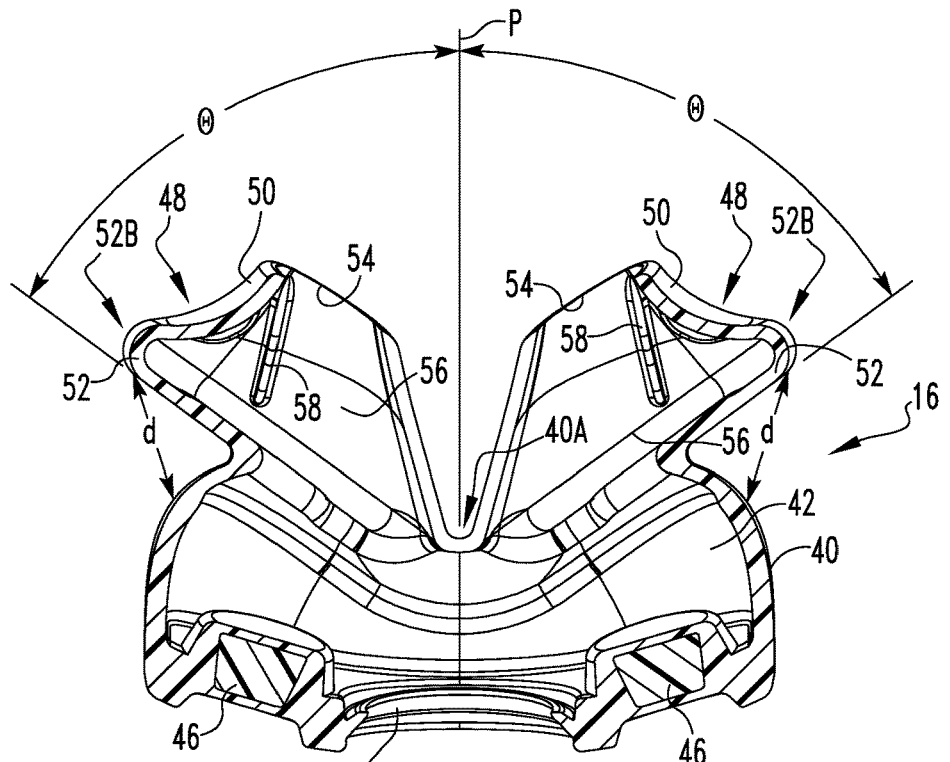
FIG. 5 is an elevation sectional view of the cushion of FIG. 1 taken along line 5-5 of FIG. 3.

As previously mentioned, each base portion 52 extends directly from base 40. More particularly, each base portion 52 includes an inner edge 52A that is positioned near the center of cushion 16 and merges with an outer surface 40A (and wall) of base 40. Each base portion 52 further includes an outer edge 52B opposite inner edge 52A that is spaced a distance d away from outer surface 40A of base 40. As shown in FIGS. 4-6, each base portion 52 is generally positioned at an angle θ relative a central reference plane P bisecting cushion 16. In example embodiments of the present invention, base portions 52 oriented at angles θ from between 30 and 135 degrees have been employed, however, angles θ of between 45 and 90 degrees have been found to generally be best for most applications. In the example embodiment illustrated in FIGS. 1-8, cushion 16 is formed as a unitary element from an elastomeric material (e.g., without limitation, silicone). However, it is to be appreciated, that cushion 16 may be formed as a modular element with components formed from any suitable material or materials without varying from the scope of the present invention.

From the foregoing example, it is thus to be appreciated that the intersection between each inner edge 52A of each base portion 52 and base 40 creates a hollow hinge that allows each cone shaped head 50 to articulate with respect to base 40 without the use of a stalk portion such a described in the Background section herein. Such intersection between base portion 52 and base 40 may be formed from a thinner amount of material than the surrounding portions and/or may be formed from a softer material to further enhance the ability of each head 50 to articulate. Such design provides for a lighter, more streamlined cushion 16 than conventional designs.

Figure 9:
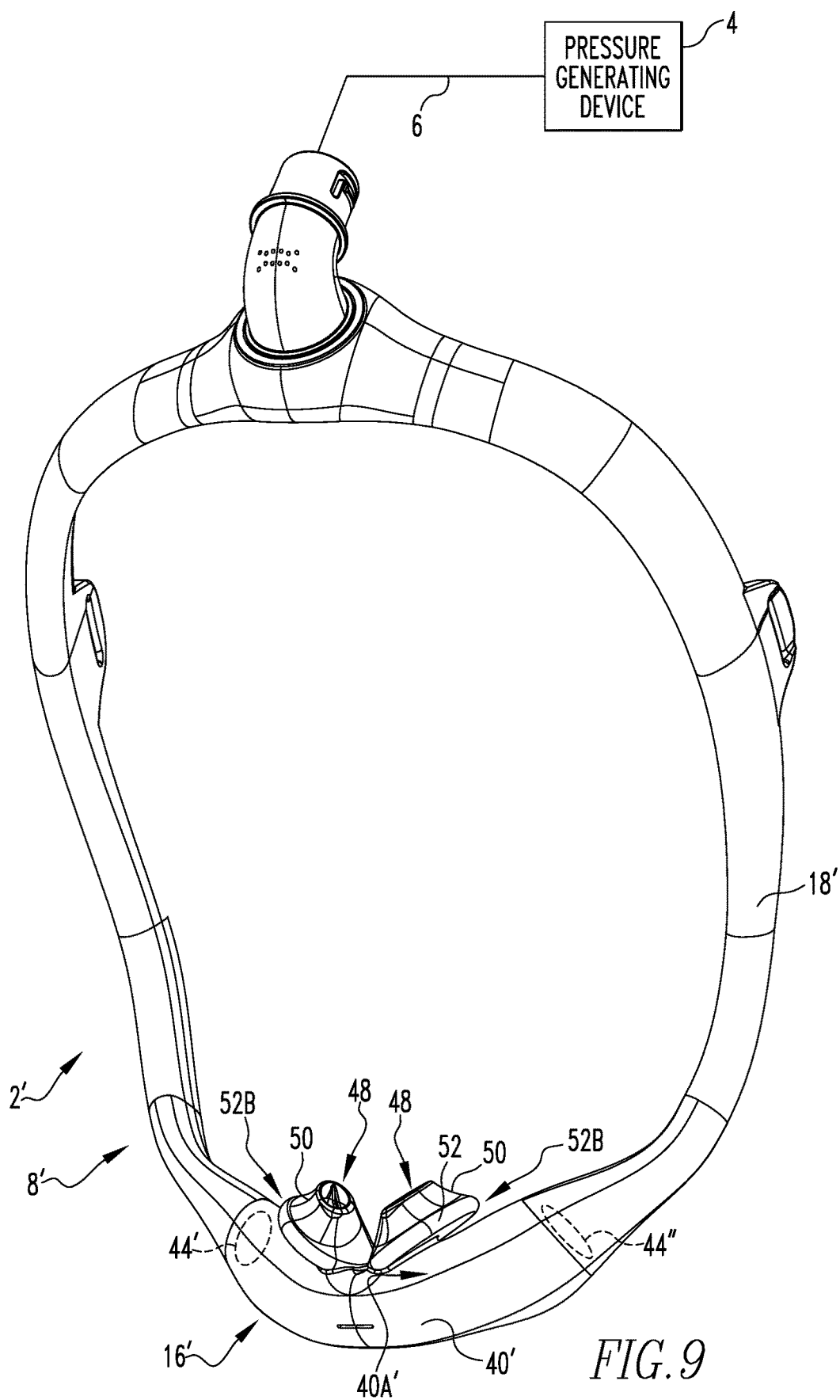
FIG. 9 is a partially schematic perspective view of another system adapted to provide a regimen of respiratory therapy to a patient including a patient interface device having another cushion according to one exemplary embodiment of the present invention.

FIG. 9 illustrates a partially schematic view of another system 2' adapted to provide a regimen of respiratory therapy to a patient that includes a patient interface device 8' having another cushion 16' according to one exemplary embodiment of the present invention. Cushion 16' is of similar construction as cushion 16 previously discussed and as such includes a generally hollow base 40' that defines a main cavity (not numbered) therein. Base 40' includes a first aperture 44', disposed at a first end of base 40' for receiving a flow of breathing gas generated by pressure generating device 4, as well as a second aperture 44", disposed at an opposite second end of base 40', that is also structured to receive a flow of breathing gas generated by pressure generating device 4. Cushion 16' further includes a pair of nasal pillows 48 like those previously discussed in regard to FIGS. 1-8 that are positioned with respect to base 40' in a similar manner as previously discussed in regard to base 40. From such further example, it is once again to be appreciated that such design provides for a lighter, more streamlined cushion 16' than conventional designs.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A cushion for use in providing a regimen of respiratory therapy to a patient, the cushion comprising: a hollow base comprising a base and a wall extending away from the [base] so as to define a main cavity therein, the base or the wall defining at least one aperture for receiving a flow of breathing gas generated by a pressure generating device; and a pair of nasal pillows each extending from the wall, each nasal pillow having a generally cone-shaped head that tapers inward and upward from a pillow base portion, that extends directly from the base, to a top opening, wherein each cone shaped head is structured to sealingly engage an inner portion of a nare of the patient with the top opening thereof positioned within the nare of the patient, wherein each cone-shaped head defines a passage there through that extends between the main cavity and the top opening and is structured to further convey the flow of breathing gas from the main cavity to a nasal passage of the patient, and wherein each pillow base portion is coupled to the wall such that a pivot point is formed between the wall and an outer portion of the pillow base portion and no such pivot point is formed between the wall and an inner edge of the pillow base portion, wherein the inner edge portion of the pillow base portion [is] located near a center of the cushion and the outer edge portion is spaced apart from the inner edge portion along a centerline of the cushion.

2. The cushion of claim 1, wherein each pillow base portion is positioned at an angle relative to a central reference plane bisecting the cushion, and wherein the angle is in the range of 45-90 degrees.

3. The cushion of claim 1, wherein the hollow base and the pair of nasal pillows are each portions of a single unitary member.

4. The cushion of claim 1, wherein a region where the inner edge of each pillow base portion and the wall merge is at least one of: a lessor thickness than a portion of the wall of the hollow base adjacent thereto or formed of a softer material than the wall adjacent thereto.

5. The cushion of claim 1, wherein the at least one aperture comprises a first aperture disposed at a first end of the wall and a second aperture disposed at an opposite second end of the wall.

6. The cushion of claim 1, wherein each cone-shaped head includes a number of ribs that each extend from an inner surface of the cone-shaped head partially into the passage defined therein.

7. A patient interface device for use in providing a regimen of respiratory therapy to a patient, the patient interface device comprising:

(a) a frame structured to be coupled to the head of the patient by a headgear; and (b) a cushion coupled to the frame, the cushion comprising:

a hollow base comprising a base and a wall extending away from the based so as to define a main cavity therein, the base or the wall defining at least one aperture for receiving a flow of breathing gas generated by a pressure generating device; and a pair of nasal pillows each extending from the wall, each nasal pillow having a generally cone-shaped head that tapers inward and upward from a pillow base portion, that extends directly from the base, to a top opening, wherein each cone shaped head is structured to sealingly engage an inner portion of a nare of the patient with the top opening thereof positioned within the nare of the patient, wherein each cone-shaped head defines a passage there through that extends between the main cavity and the top opening and is structured to further convey the flow of breathing gas from the main cavity to a nasal passage of the patient, and wherein each pillow base portion is coupled to the wall such that a pivot point is formed between the wall and an outer portion of the pillow base portion and no such pivot point is formed between the wall and an inner edge of the pillow base portion, wherein the inner edge portion of the pillow base portion in located near a center of the cushion and the outer edge portion is spaced apart from the inner edge portion along a centerline of the cushion.

8. The patient interface device of claim 7, wherein each pillow base portion is positioned at an angle relative to a central reference plane bisecting the cushion, and wherein the angle is in the range of 45-90 degrees.

9. The patient interface device of claim 7, wherein the hollow base and the pair of nasal pillows are each portions of a single unitary member.

10. The patient interface device of claim 7, wherein a region where the inner edge of each pillow base portion and the wall merge is at least one of: a lessor thickness than a portion of the wall of the hollow base adjacent thereto or formed of a softer material than the wall adjacent thereto.

11. The patient interface device of claim 7, wherein the at least one aperture comprises a first aperture disposed at a first end of the wall and a second aperture disposed at an opposite second end of the wall.

12. The patient interface device of claim 7, wherein each cone-shaped head includes a number of ribs that each extend from an inner surface of the cone-shaped head partially into the passage defined therein.

13. A system adapted to provide a regimen of respiratory therapy to a patient, the system comprising: (a) a pressure generating device structured to generate a flow of breathing gas; (b) a delivery conduit having a first end coupled to the pressure generating device and an opposite second end; and (c) a patient interface device comprising: a frame structured to be coupled to the head of the patient by a headgear; and a cushion coupled to the frame, the cushion comprising: a hollow base comprising a base and a wall extending away from the [base] so as to define a main cavity therein, the base or the wall defining at least one aperture for receiving a flow of breathing gas generated by a pressure generating device; and a pair of nasal pillows each extending from the wall, each nasal pillow having a generally cone-shaped head that tapers inward and upward from a pillow base portion, that extends directly from the base, to a top opening, wherein each cone shaped head is structured to sealingly engage an inner portion of a nare of the patient with the top opening thereof positioned within the nare of the patient, wherein each cone-shaped head defines a passage there through that extends between the main cavity and the top opening and is structured to further convey the flow of breathing gas from the main cavity to a nasal passage of the patient, and wherein each pillow base portion is coupled to the wall such that a pivot point is formed between the wall and an outer portion of the pillow base portion and no such pivot point is formed between the wall and an inner edge of the pillow base portion, wherein the inner edge portion of the pillow base portion [is] located near a center of the cushion and the outer edge portion is spaced apart from the inner edge portion along a centerline of the cushion.

14. The system of claim 13, wherein each pillow base portion is positioned at an angle relative to a central reference plane bisecting the cushion, and wherein the angle is in the range of 45-90 degrees.

15. The system of claim 13, wherein the hollow base and the pair of nasal pillows are each portions of a single unitary member.

16. The system of claim 13, wherein a region where the inner edge of each pillow base portion and the wall merge is at least one of: a lessor thickness than a portion of the wall of the hollow base adjacent thereto or formed of a softer material than the wall adjacent thereto.

17. The system of claim 13, wherein the at least one aperture comprises a first aperture disposed at a first end of the wall and a second aperture disposed at an opposite second end of the wall.

18. The system of claim 13, wherein each cone-shaped head includes a number of ribs that each extend from an inner surface of the cone-shaped head partially into the passage defined therein.

* * * * *